(12) United States Patent
Noritake et al.

(10) Patent No.: US 7,261,862 B2
(45) Date of Patent: Aug. 28, 2007

(54) LIQUID DROP EMITTER

(75) Inventors: Motoo Noritake, Ichinomiya (JP);
Toshikazu Hirota, Nagoya (JP); Takao Ohnishi, Aichi-Prefecture (JP)

(73) Assignee: NGK Insulators, Ltd., Nagoya (JP)

( * ) Notice: Subject to any disclaimer, the term of this patent is extended or adjusted under 35 U.S.C. 154(b) by 471 days.

(21) Appl. No.: 10/229,910

(22) Filed: Aug. 28, 2002

(65) Prior Publication Data
US 2003/0054541 A1 Mar. 20, 2003

(30) Foreign Application Priority Data
Aug. 31, 2001 (JP) .............................. 2001-263923

(51) Int. Cl.
*B41J 2/145* (2006.01)
(52) U.S. Cl. .................... 422/100; 347/41; 347/68; 347/71; 347/85; 347/87
(58) Field of Classification Search ............... 422/100; 436/180; 347/41, 68–72, 85–87
See application file for complete search history.

(56) References Cited

U.S. PATENT DOCUMENTS

| 5,748,214 | A | * | 5/1998 | Usui et al. ................ 347/70 |
| 6,557,985 | B2 | * | 5/2003 | Hosono et al. ............. 347/70 |
| 6,814,937 | B1 | * | 11/2004 | Hirota et al. ............... 422/100 |
| 6,852,545 | B2 | * | 2/2005 | Hirota et al. ............... 436/180 |
| 2001/0022596 | A1 | * | 9/2001 | Korol ....................... 347/10 |
| 2001/0024221 | A1 | * | 9/2001 | Tanaka et al. .............. 347/68 |
| 2002/0018095 | A1 | * | 2/2002 | Nakamura et al. .......... 347/40 |
| 2002/0167569 | A1 | * | 11/2002 | Hosono et al. ............. 347/70 |

FOREIGN PATENT DOCUMENTS

| JP | 2001-124789 A1 | 5/2001 |
| JP | 2001-186880 A1 | 7/2001 |
| WO | WO 00/24511 | 5/2000 |
| WO | WO 02/34379 | 5/2002 |

* cited by examiner

Primary Examiner—Jan M. Ludlow
(74) Attorney, Agent, or Firm—Burr & Brown

(57) ABSTRACT

An improved structure of a liquid drop emitter is provided which works to emit minute drops of liquid to deposit them in a dense array of dots on a substrate to produce a DNA chip, for example. The liquid drop emitter has a plurality of liquid inlets formed in rows in a staggered fashion, thereby allowing the liquid inlets to have a maximum possible area without any physical interference between adjacent two of them and also allowing outlet nozzles to be arranged in a dense array.

8 Claims, 11 Drawing Sheets

LIQUID DROP EMITTER

BACKGROUND OF THE INVENTION

1. Technical Field of the Invention

The present invention relates generally to an improved structure of a liquid drop emitter, and more particularly to a liquid drop emitter designed to emit a plurality of minute drops of liquid and deposit them on a substrate in a dense array of dots to produce a DNA chip, for example.

2. Background Art

In recent years, rapid progress has been made in analyzing gene structure. Various kinds of gene structures as well as human gene structures have been found. Such gene analysis usually uses a DNA chip on which more than a few thousand types of DNA fragments are deposited and immobilized in an array of minute spots.

Such deposition on the DNA chip is typically achieved using a quill mechanism, a pin-ring mechanism, or a spring pin mechanism. In either case, improvement of productivity of DNA chips, i.e., increasing of speed of production thereof and increasing of accuracy of encoding DNA information are sought. Such increasing of accuracy requires uniformity of quantity and concentration of drops of liquid containing DNA fragments.

Typical DNA chip production uses a liquid drop emitter which includes a plurality of micropipettes each consisting of a liquid inlet, a liquid sump, a compression chamber, an outlet nozzle. The micropipettes are arranged in parallel to each other. A liquid inlet and a discharge nozzle are arranged in one line toward the base body. The actuator that compresses the liquid inside of the compression chambers is located outside the compression chambers in such a liquid drop emitter. For example, a piezoelectric/electrostrictive element is used as this actuator.

In order to increase the speed and efficiency of production of DNA chips using the above type of liquid drop emitter, it is necessary to decrease the size of the micropipettes and arrange them close to each other to provide as many outlet nozzles as possible per unit area. In other words, it is the plan that DNA chip manufacture be sped up by closely arranging the discharge nozzles so that many drops may be formed on slide glass.

SUMMARY OF THE INVENTION

It is therefore a principal object of the invention to avoid the disadvantages of the prior art.

It is another object of the invention to provide a liquid drop emitter capable of emitting minute drops of liquid and depositing them in a dense array on a substrate.

According to one aspect of the invention, there is provided a liquid drop emitter which may be employed in a liquid depositing system to deposit minute drops of liquid containing DNA fragments on a substrate in a dense array of dots to produce a DNA chip. The liquid drop emitter comprises: (a) a plurality of micropipettes arrayed parallel to each other, each of the micropipettes defining a liquid flow path extending from a liquid inlet to an outlet nozzle through a liquid sump and a compression chamber to emit a drop of liquid; and (b) actuators each of which works to compress a volume of one of the compression chambers to achieve emission of the drop of liquid from one of the outlet nozzles. The liquid inlets are arrayed in rows in a staggered fashion, thereby allowing the liquid inlets to have a maximum possible area without any physical interference between adjacent inlets and also allowing the outlet nozzles to be arranged in a dense array.

In the preferred mode of the invention, the micropipettes are provided in the same body.

The liquid flow paths of the micropipettes are identical in volume with each other.

Portions of the liquid flow paths of the micropipettes extending from inlets of the compression chambers to the outlets nozzles are identical in volume with each other, thereby enabling a plurality of drops of liquid which are identical in quantity to be emitted from the outlet nozzles using the actuators of the same structure.

The liquid sumps of adjacent two of the micropipettes may be different in width from each other.

The liquid sumps of adjacent two of the micropipettes may alternatively be different in depth from each other.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
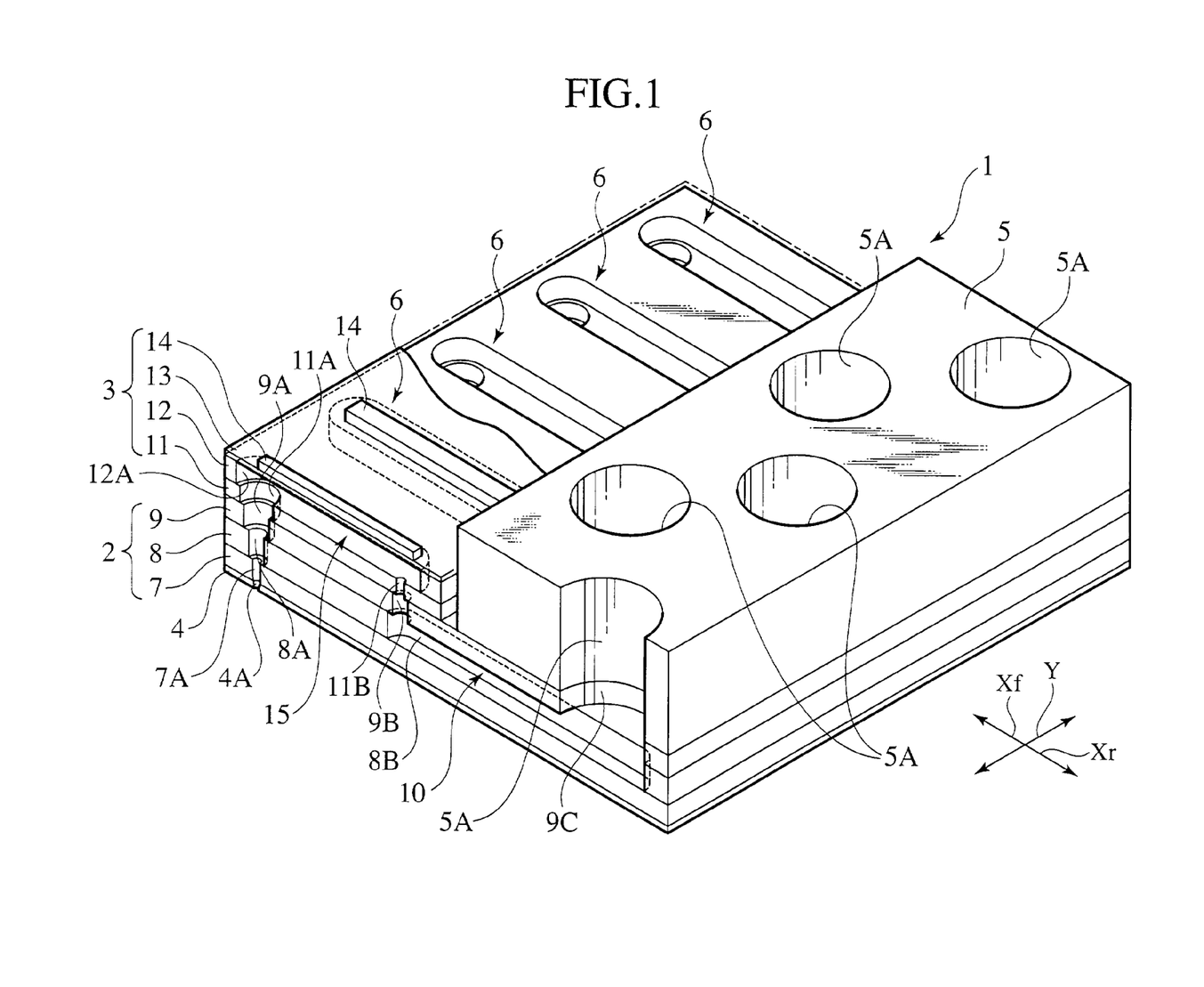
FIG. 1 is a perspective view which shows a liquid drop emitter according to the first embodiment of the invention.

Referring to the drawings, wherein like reference numbers refer to like parts in several views, particularly to FIG. 1, there is shown a liquid drop emitter 1 according to the first embodiment of the invention which is suited to emit drops of liquid containing DNA fragments and deposit them on a substrate in a dense array of dots. The liquid drop emitter 1, as will be described below in detail, features liquid inlets arranged in rows in a staggered fashion in order to provide a dense array of nozzles and/or a compact overall structure without sacrificing the size of an opening of each of the liquid inlets.

The liquid drop emitter 1 consists essentially of a flow-path base plate 2, an actuator assembly 3, a nozzle plate 4, and a liquid inlet block 5. The flow-path base plate 2 has a plurality of flow paths formed therein. The actuator assembly 3 is installed on the flow-path base plate 2 and, as will be described later in detail, works to change volumes of compression chambers to emit minute drops of liquid. The nozzle plate 4 is attached to the bottom of the flow-path base plate 2 and has outlet nozzles 4A formed therein. The liquid inlet block 5 is disposed on an upper rear surface of the flow-path base plate 2 (i.e., on the right side, as viewed in the drawing). The liquid drop emitter 1 also has a plurality of micropipettes 6 arrayed, as clearly shown in FIG. 2, at given intervals in parallel in a widthwise direction (will also be referred to as a Y-direction below) of the body of the liquid drop emitter 1.

The flow-path base plate 2 is made of a laminate of a lower layer 7 to which the nozzle plate 4 is attached, a middle layer 8, and an upper layer 9. The layers 7, 8, and 9 are formed by laying green sheets made of a ceramic material such as zirconia to overlap each other and firing them.

Figure 4:
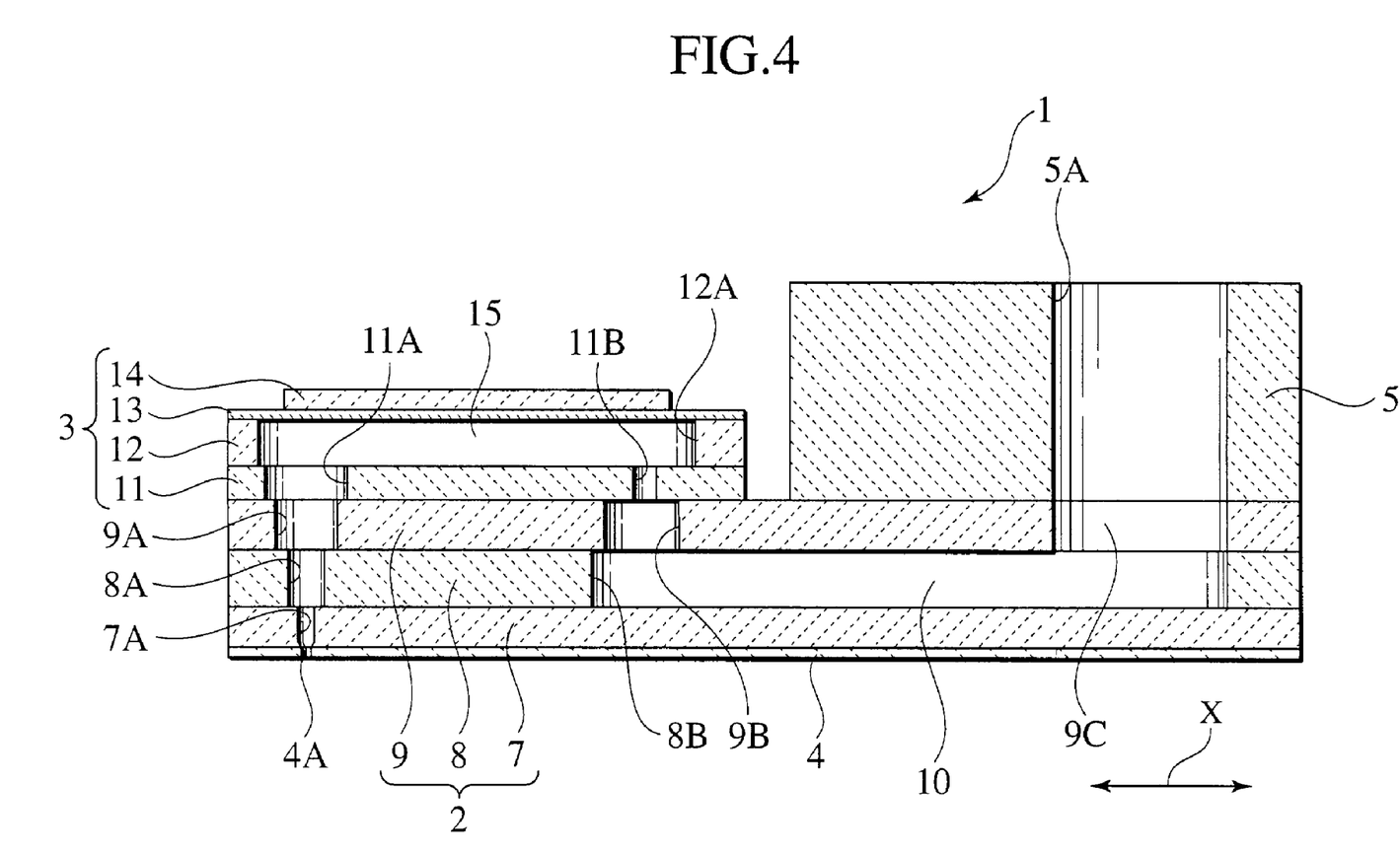
FIG. 4 is a vertical sectional view taken along the line A-A in FIG. 2.
Figure 5:
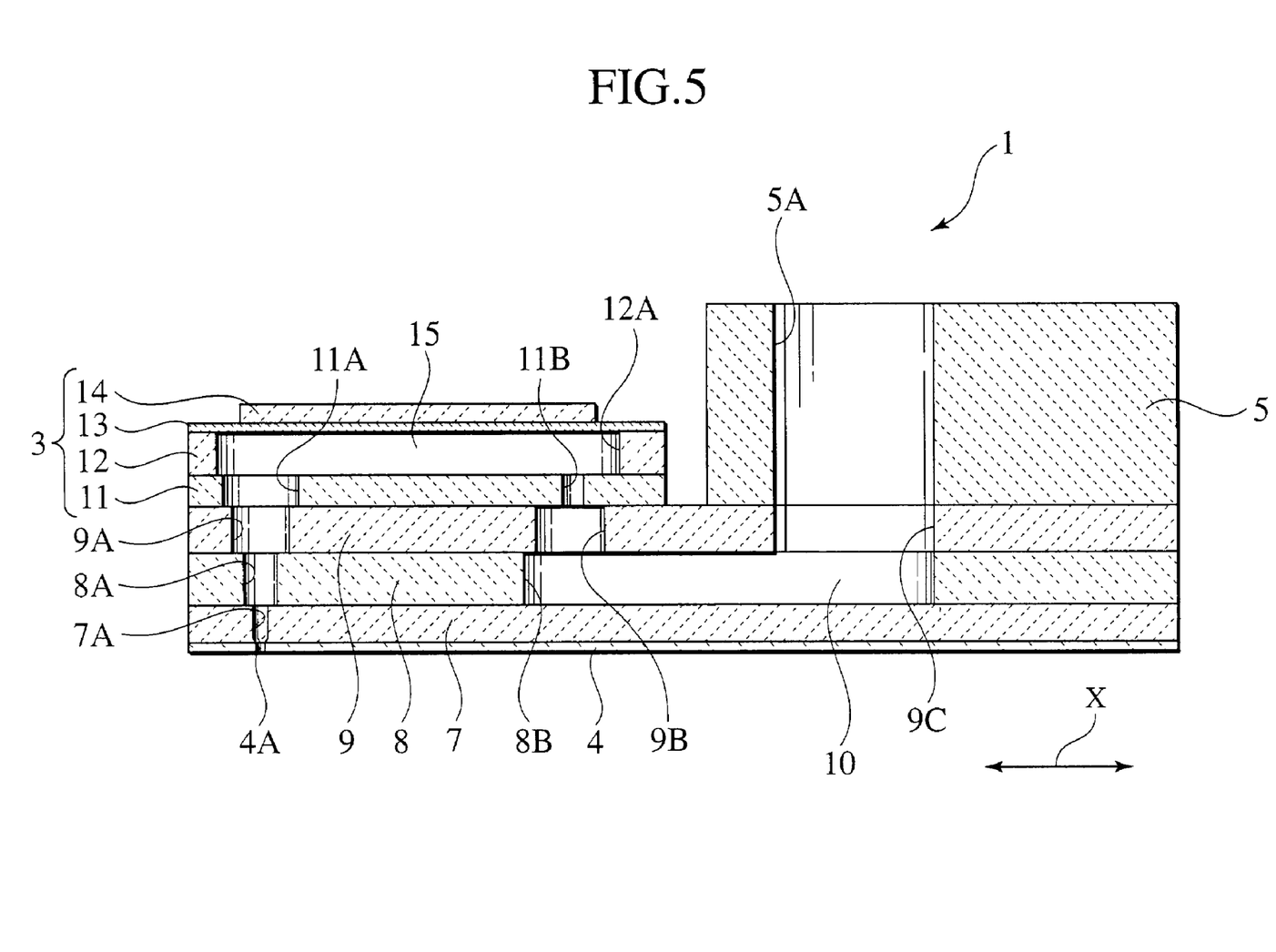
FIG. 5 is a vertical sectional view taken along the line B-B in FIG. 2.

The lower layer 7 has, as clearly shown in FIGS. 1, 4, and 5, a plurality of liquid outlets 7A formed in a front end portion thereof (i.e., a left end portion as viewed in FIGS. 4 and 5). The liquid outlets 7A are arrayed at given intervals in the Y-direction and communicate with the outlet nozzles 4A of the nozzle plate 4, respectively.

The middle layer 8 has a plurality of flow holes 8A formed in a front end portion thereof in alignment with the liquid outlets 7A of the lower layer 7. The flow holes 8A communicate with the liquid outlets 7A, respectively, and are greater in diameter than them. The middle layer 8 also has a plurality of elongated holes 8B each formed on a rear side of one of the flow holes 8A in an Xr-direction, as indicated in FIG. 1. The elongated holes 8B define liquid sumps 10 between the upper and lower layers 9 and 7. Each of the liquid sumps 10 is different in length and width from an adjacent one, which will be discussed later in detail.

The upper layer 9 has a plurality of flow holes 9A formed in a front end portion thereof (i.e., an Xf-direction in FIG. 1) in alignment with the flow holes 8A of the middle layer 8. The flow holes 9A communicate with the flow holes 8A, respectively, and are greater in diameter than them. The upper layer 9 also has formed therein flow holes 9B and 9C. Each of the flow holes 9B communicates with a downstream end of one of the liquid sumps 10. Each of the flow holes 9C communicates with an upstream end of one of the liquid sumps 10.

The lower layer 7, the middle layer 8, and the upper layer 9 are, as described above, made of a ceramic material. For instance, stabilized zirconia, partially stabilized zirconia, alumina, magnesia, or silicon nitride may be used. Of these, the stabilized zirconia and partially stabilized zirconia are preferable in terms of mechanical strength and toughness.

The actuator assembly 3 is made up of a bottom plate 11, a cavity-forming plate 12, a diaphragm 13, and piezoelectric/electrostrictive devices 14. The bottom plate 11 is disposed on a front half of the upper surface of the upper layer 9 of the flow-path base plate 2. The diaphragm 13 covers the cavity-forming plate 12. The cavity-forming plate 12 is disposed on the bottom plate 11 and has formed therein elongated holes 12A which define cavities 15 between the bottom plate 11 and the diaphragm 11. The cavities 15 work as compression chamber for discharging drops of liquid from the outlet nozzles 4A. The piezoelectric/electrostrictive devices 14 are mounted on the upper surface of the diaphragm 13 and work as actuators which press the diaphragm 13 to change the volume of the cavities 15.

The bottom plate 11 has formed therein flow holes 11A and 11B formed therein coaxially in alignment with the flow holes 9A and 9B of the upper layer 9 of the flow-path base plate 2. The flow holes 11A communicate with the flow holes 9A, respectively, and are greater in diameter than them. The flow holes 11B communicate with the flow holes 9B, respectively, and are smaller in diameter than them. The flow holes 11A and 11B communicate with each other through the cavities 15. The diaphragm 13 is made of a rectangular thin plate which covers the whole of the upper surface of the cavity-forming plate 12.

The bottom plate 11, the cavity-forming plate 12, and the diaphragm 13 are each made by firing a ceramic green sheet which is of the same material as the flow-path base plate 2. Specifically, stabilized zirconia, partially stabilize zirconia, alumina, magnesia, or silicon nitride may be used. Of these, the stabilized zirconia and partially stabilized zirconia are suitable for the diaphragm 13 in terms of mechanical strength and toughness and most preferable because it is lower in reaction with a piezoelectric film or an electrode. In a case where the diaphragm 13 is made of stabilized zirconia or partially stabilized zirconia, it is advisable that an at least portion of the diaphragm on which the piezoelectric/electrostrictive devices 14 are mounted contain an additive of alumina or titanium.

Each of the piezoelectric/electrostrictive devices 15 is formed by a laminate of piezoelectric/electrostrictive layers each made of a ceramic material which contains one or a mixture of lead zirconate, lead titanate, lead mnagnesium-niobate, lead manganese tantalate, lead nickel niobate, lead zinc niobate, lead manganese niobate, lead antimony stannate, lead manganese tungstate, lead cobalt niobate, and barium titanate. These are lower in reaction with firing of a piezoelectric film as well as having high electromechanical coupling factor and piezoelectric constant. The piezoelectric/electrostrictive devices 15 have a known structure, and details thereof such as electrode pads are omitted here.

Figure 2:
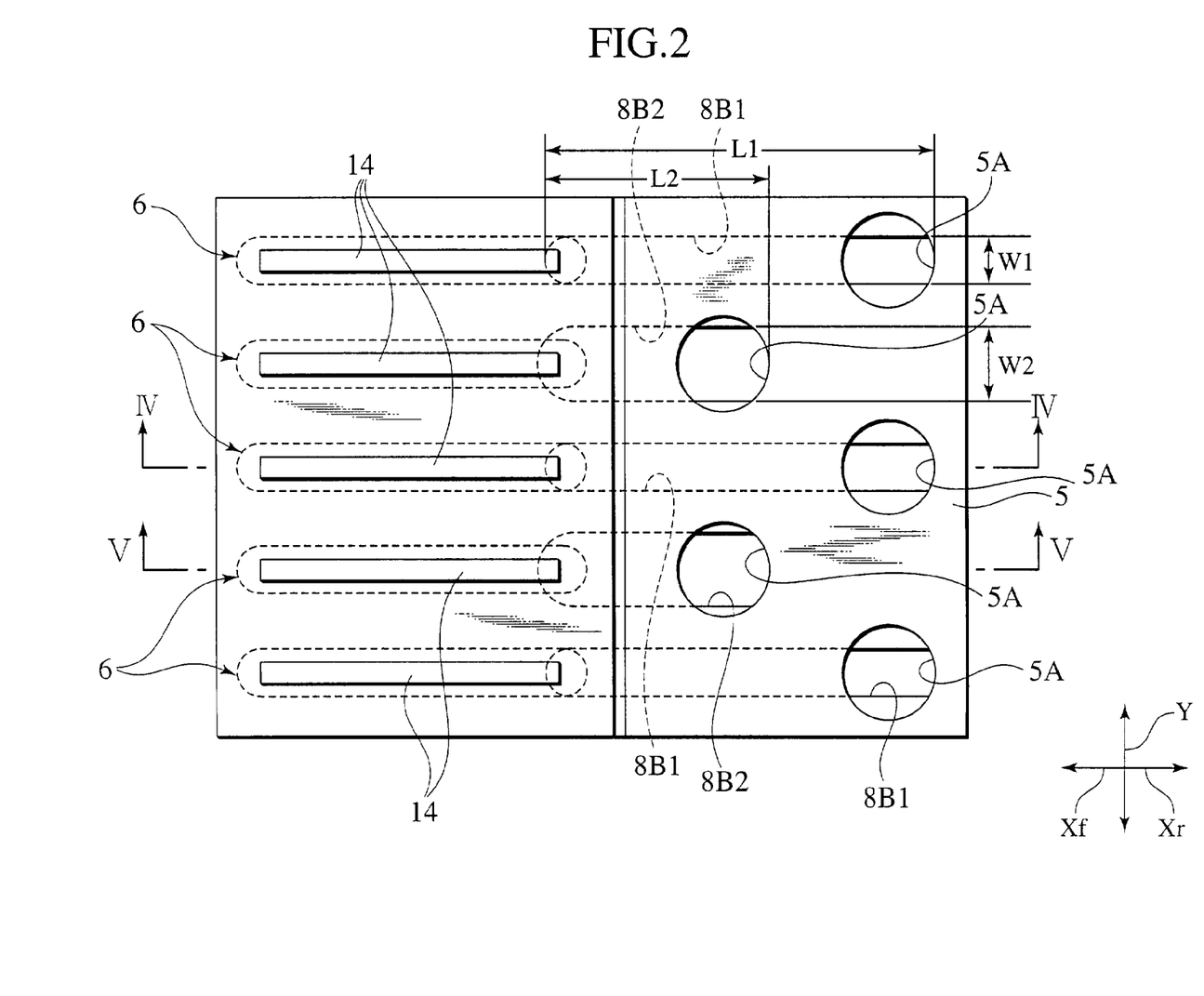
FIG. 2 is a top view which shows the liquid drop emitter of FIG. 1.

The elongated holes 8B formed in the middle layer 8 of the flow-path base plate 2 are, as can be seen from FIG. 2, broken down into two groups. The first group is made up of the elongated holes 8B1 each having a greater length L1 and a smaller width W1. The second group is made up of the elongated holes 8B2 each having a smaller length L2 and a greater width W2. One of adjacent two of the micropipettes 6, as clearly shown in the drawing, includes one of the elongated holes 8B1, and the other includes one of the elongated holes 8B2. The elongated holes 8B1 and 8B2 all have the same depth which corresponds to the thickness of the middle layer 8. The liquid sumps 10 defined by the elongated holes 8B1 are substantially identical in volume with those defined by the elongated holes 8B2. Therefore, all the micropipettes 6 extending from the liquid inlets 5A to the outlet nozzles 4A have substantially the same volume, thereby enabling a plurality of drops of liquid which are identical in quantity to be emitted from the outlet nozzles 4A using the piezoelectric/electrostrictive devices 14 of the same structure and also permitting all the micropipettes 6 to be refilled with liquid simultaneously, thus ensuring high efficiency of the liquid drop-emitting operation and the refilling operation.

The flow holes 9C of the upper layer 9 are located just above the rear ends (i.e., upstream ends) of the elongated holes 8B1 and 8B2 and, as can be seen from FIG. 1, arrayed in two rows in a staggered fashion in the Y-direction.

The liquid inlet block 5 is, as described above, secured on a rear half of the upper surface of the flow-path base plate 2. The liquid inlet block 5 is of a substantially rectangular parallelepiped shape and located adjacent the rear end of the actuator assembly 3. The liquid inlet block 5 has liquid inlets 5A formed in two rows in a staggered fashion each of which leads to one of the flow holes 9C of the upper layer 9 of the flow-path base plate 2. The liquid inlets 5A may alternatively be arrayed alternately in the X-direction (i.e., the widthwise direction of the body of the liquid drop emitter 1) in more than two rows. The liquid inlets 5A are all identical in diameter and depth with each other. The liquid inlet block 5 is made of, for example, polypropylene, acrylic or stainless steel or same ceramic material as that of the base plate 2 and actuator assembly 3.

Figure 3:
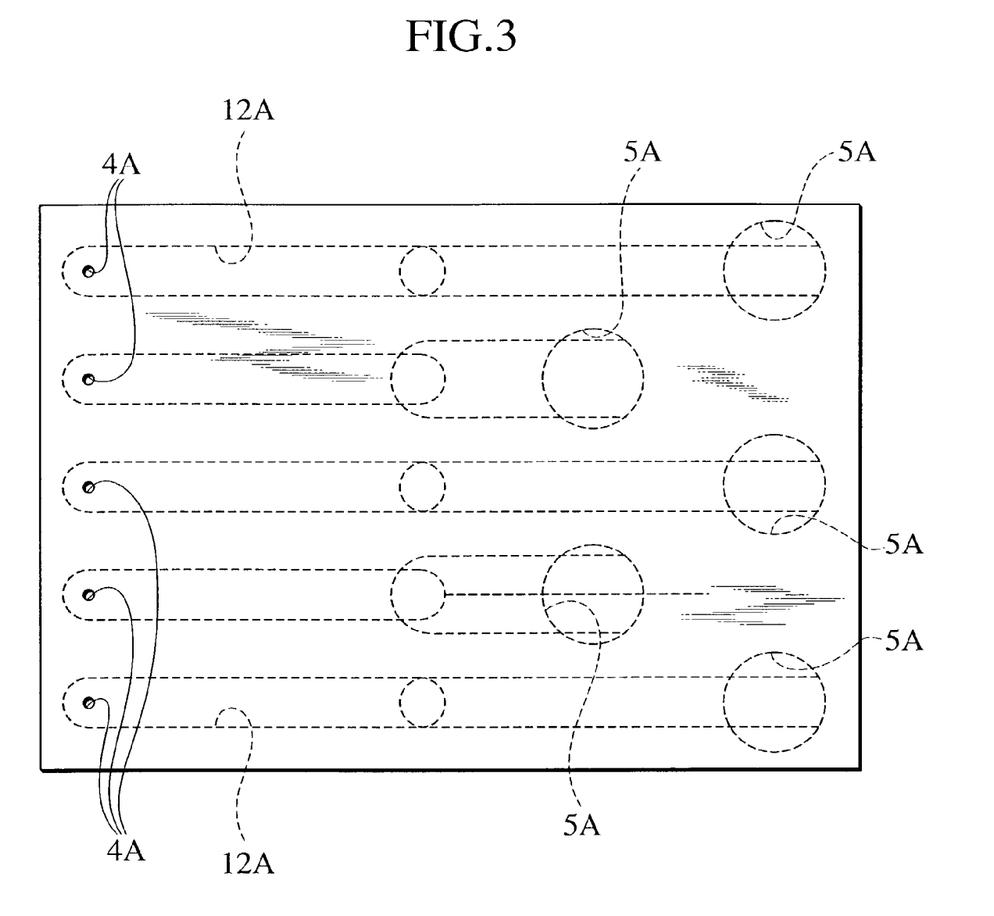
FIG. 3 is a bottom view which shows the liquid drop emitter of FIG. 1.

The nozzle plate 4 is made of, for example, polyester (PET) film, stainless steel (SUS304), alumina, or partially stabilized zirconia (PSZ). The nozzle plate 4 is bonded with, for example, epoxy bonding film (thermosetting), polyethylene bonding film (thermoplastic). The nozzle plate 4, as already described, has formed therein the outlet nozzles 4A each of which communicates with one of the liquid outlets 7A formed in the lower layer 7 of the flow-path base plate 2. The outlet nozzles 4A are, as clearly shown in FIG. 3, arrayed in line in the vertical direction of the nozzle plate 4. As apparent from the above discussion, the liquid inlets 5A, the flow holes 9C, the liquid sumps 10, the flow holes 9B and 11B, the cavities 15, the flow holes 11A, 9A, and 8A, the liquid outlets 7A, and the outlet nozzles 4A form the micropipettes 6, respectively.

Production processes of a DNA chip will be described below.

Figure 6:
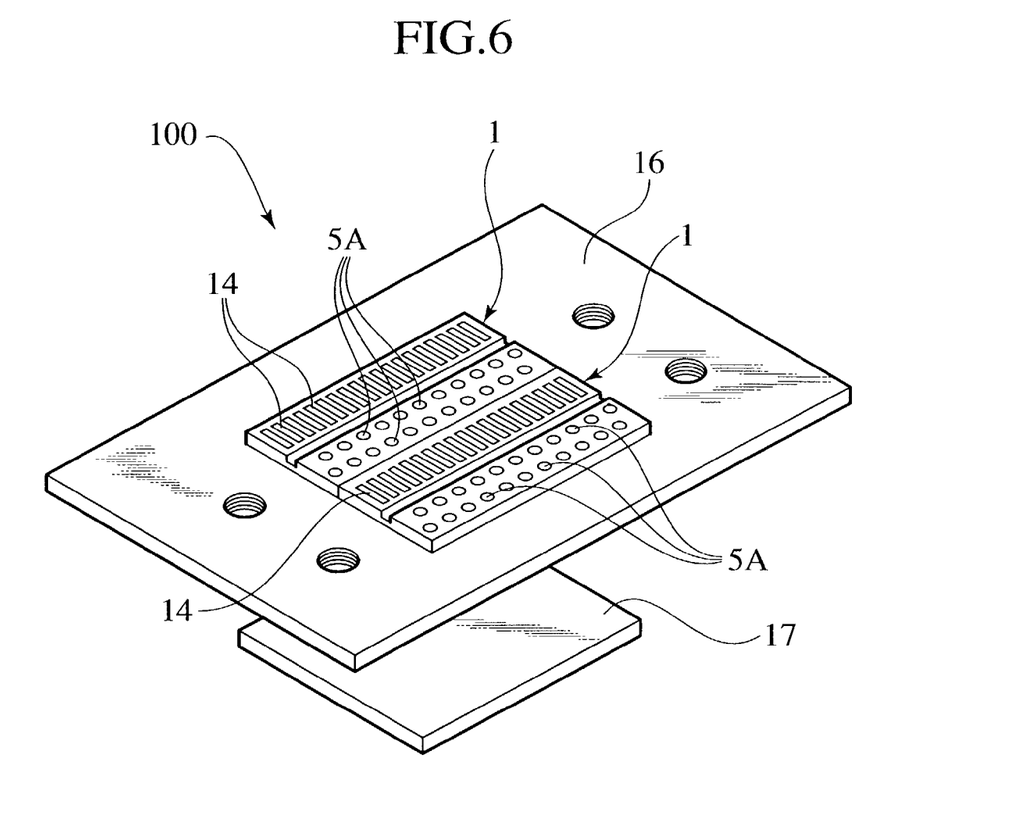
FIG. 6 is a perspective view which shows a liquid depositing unit using two liquid drop emitters having the same structure as the one shown in FIG. 1.

FIG. 6 illustrates a liquid depositing unit 100 made up of the two liquid drop emitters 1 installed in parallel on a mount plate 16 to provide two arrays of the outlet nozzles 4A.

Figure 7:
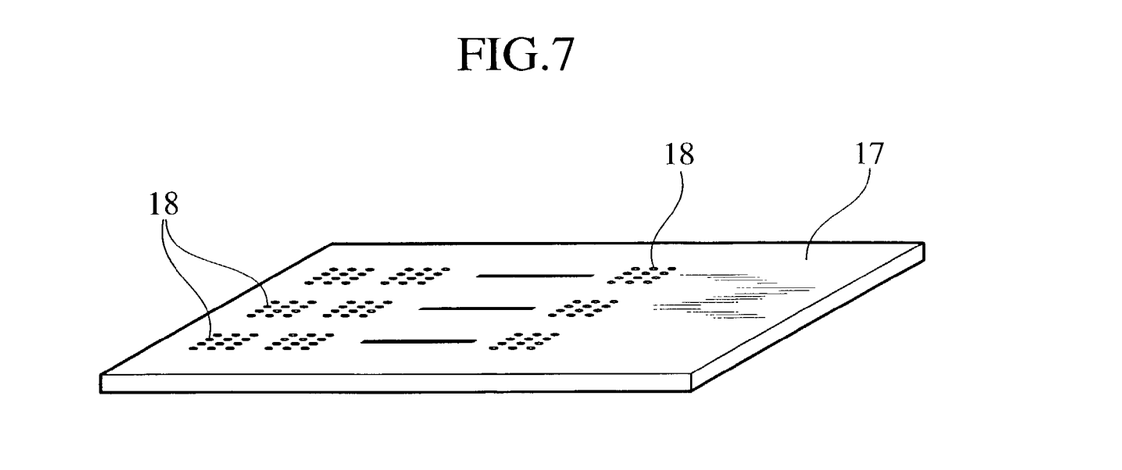
FIG. 7 is a perspective view which shows a slide glass on which drops of liquid containing DNA fragments are deposited to produce a DNA chip.

First, the liquid depositing unit 100 is placed above a slide glass 17. Next, the piezoelectric/electrostrictive devices 14 of the actuator assembly 3 are energized to compress the volumes of the cavities 15 through the diaphragm 13, thereby emitting minute drops of liquid from the outlet nozzles 4A to deposit them. The minute drops of liquid 18 are formed in the fixed interval as shown in FIG. 7 on slide glass 17.

The structure of the liquid drop emitter 1 of this embodiment as described above, features the staggered arrangement of the liquid inlets 5A, which allows the liquid inlets 5A to have a maximum possible area without any physical interference between adjacent inlets, thus facilitating ease with which an operator puts liquid containing DNA fragments into the liquid inlets 5A and ensuring a desired quantity of the liquid emitted from each of the outlet nozzles 4A. Such a staggered arrangement also permits the micropipettes 6 to be formed in a dense array within the body of the liquid drop emitter 1 without sacrificing the size of an opening of each of the liquid inlets 5A.

The liquid drop emitter 1 of this embodiment has the plurality of micropipettes 6 formed in the same flow-path base plate 2, thereby increasing the locational accuracy of the micropipettes 6 and resulting in a decreased size of the liquid drop emitter 1 as compared with a case where micropipettes are made independently and arrayed adjacent each other.

Further, the liquid drop emitter 1 has total volumes of the micropipettes 6 from the liquid inlets 5A to the outlet nozzles 4A identical with each other, thereby allowing the same volume of liquid to be stored in the micropipettes 6. This permits the piezoelectric/electrostrictive devices 14 working as actuators to have the same performance and the outlet nozzles 4A to have the same dimension such as diameter for refilling all the micropipettes 6 with substantially the same timing. For example, it becomes possible in DNA chip production to perform liquid drop emitting and liquid refilling operations effectively.

The volumes of portions of the flow paths (i.e., the micropipettes 6) extending from inlets of the cavities 15 to the outlet nozzles 4A are identical with each other, thus allowing the same quantity of drops of liquid to be emitted from the outlet nozzles 4A using the piezoelectric/electrostrictive devices 15 having the same structure.

Further, the adjacent micropipettes 6 have the same total volumes from the liquid inlets 5A leading to the liquid sumps 10 whose widths are different from each other to the outlet nozzles 4A, thus allowing the liquid sumps 10 to be arranged so as to have different lengths. This ensures a desired open area of the liquid inlets 5A without physical interference therebetween.

Figure 8:
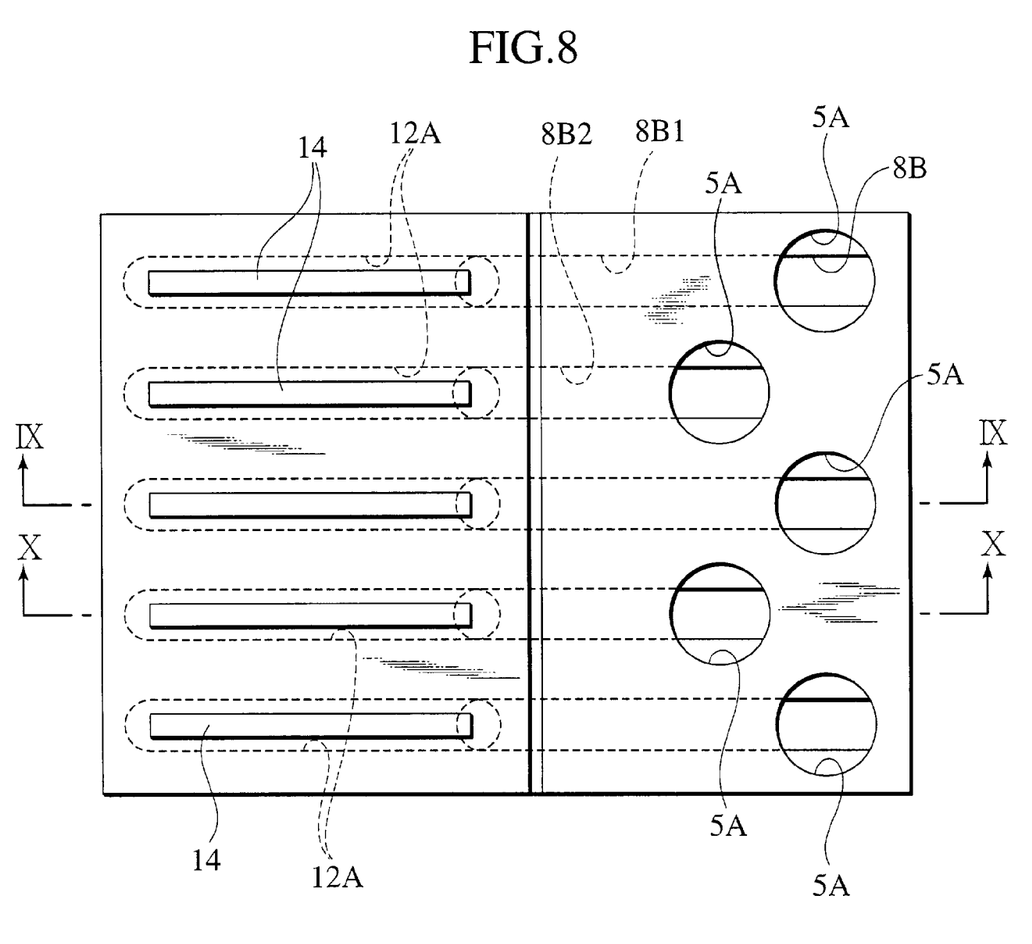
FIG. 8 is a top view which shows a liquid drop emitter according to the second embodiment of the invention.
Figure 9:
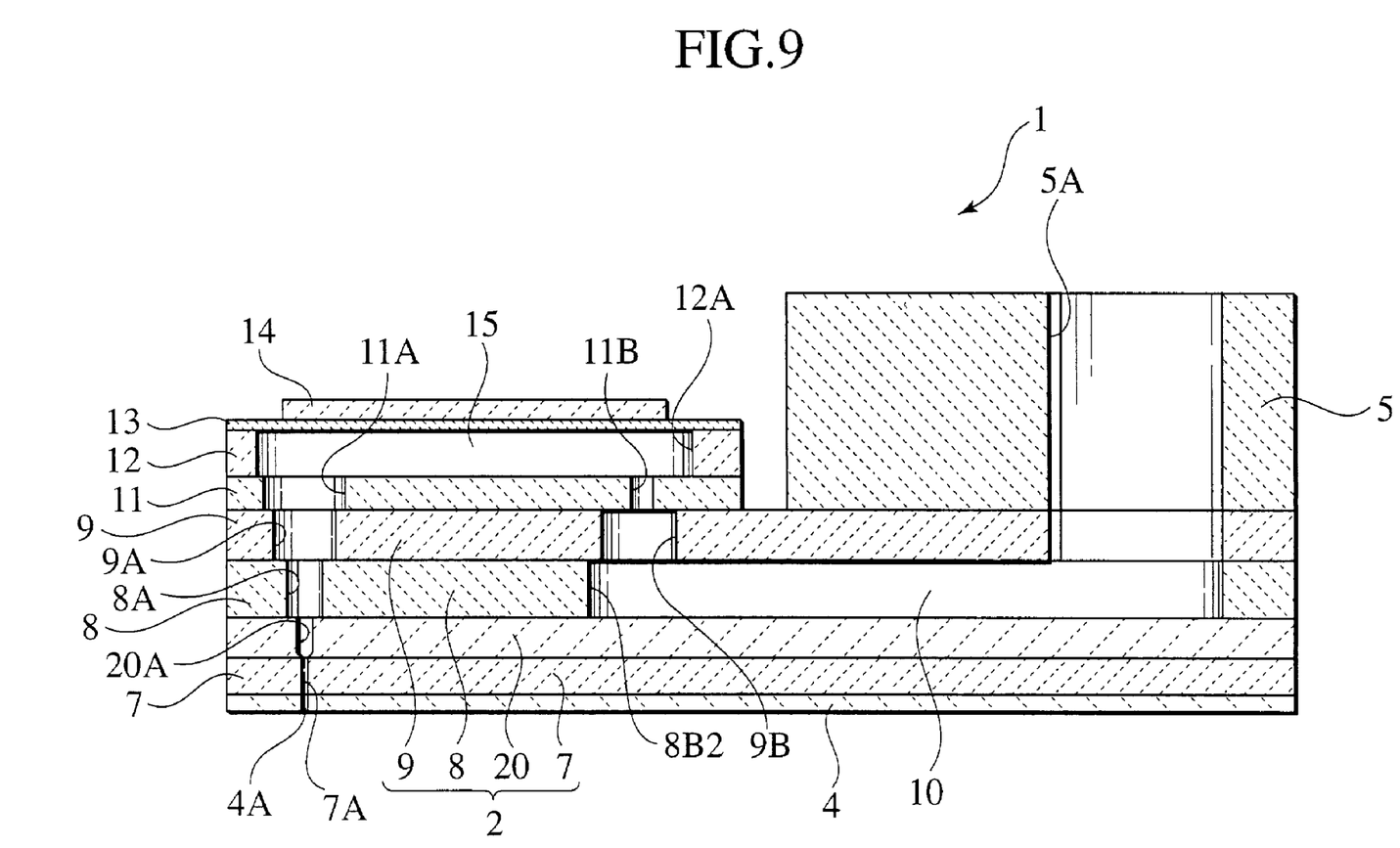
FIG. 9 is a vertical sectional view taken along the line C-C in FIG. 8.
Figure 10:
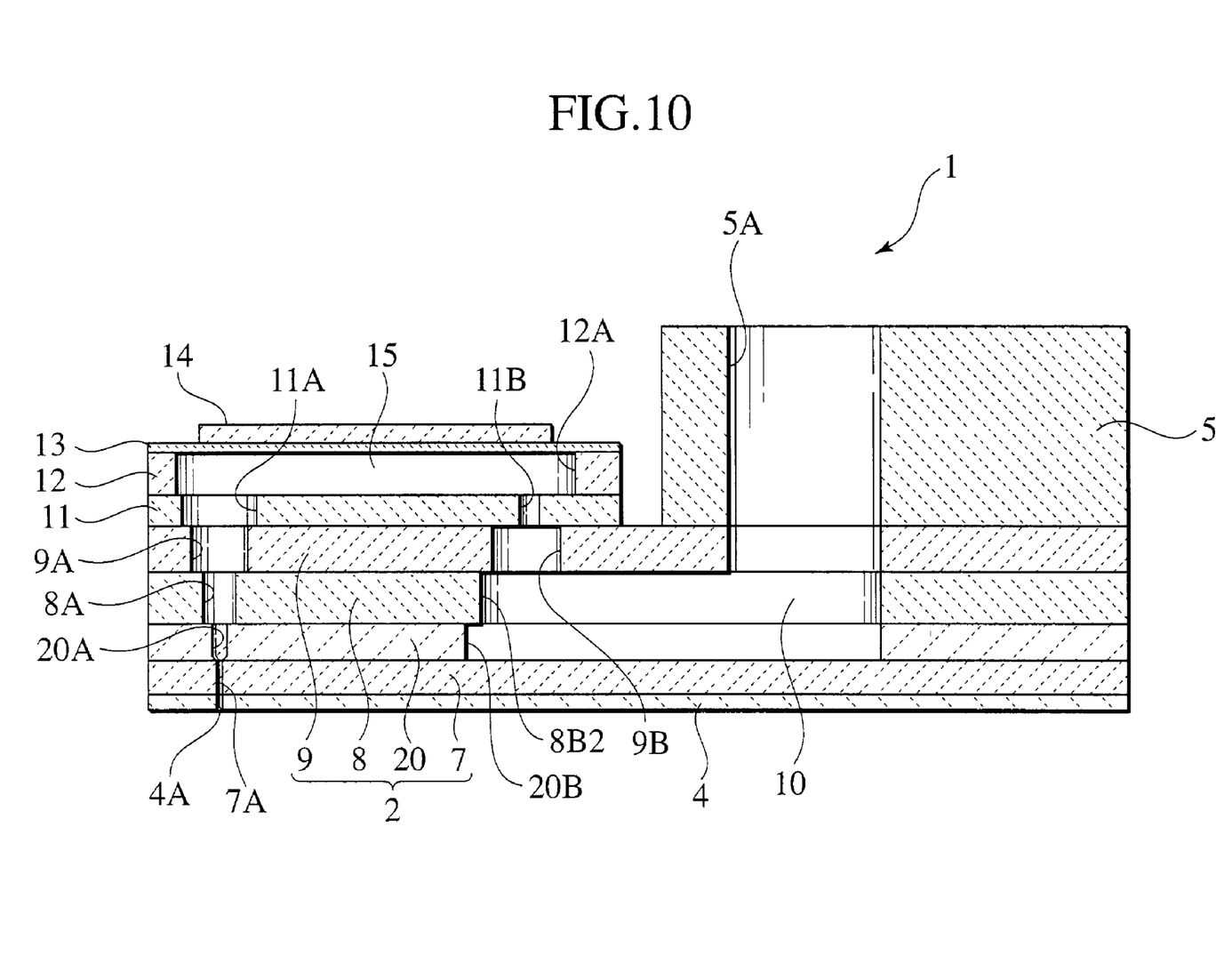
FIG. 10 is a vertical sectional view taken along the line D-D in FIG. 8.

FIGS. 8 to 10 show the liquid drop emitter 1 according to the second embodiment of the invention. The same reference numbers as employed in the first embodiment will refer to the same parts, and explanation thereof in detail will be omitted here.

The flow-path base plate 2 of this embodiment, as clearly shown in FIGS. 9 and 10, includes a spacer 20 in addition to the lower layer 7, the middle layer 8, and the upper layer 9. The spacer 20 is interposed between the lower layer 7 and the middle layer 8 and has formed therein flow holes 20A identical in structure with the liquid outlets 7A in the first embodiment. The flow holes 20A communicate with the flow holes 8A and the liquid outlets 7A, respectively. The spacer 20 also has, as shown in FIG. 10, elongated holes 20B formed just below the shorter elongated holes 8B2, respectively, to define some of the liquid sumps 10 having a greater depth. The spacer 20, as clearly shown in FIG. 9, has no holes just below the longer elongated holes 8B1 to define the remaining liquid sumps 10 having a smaller depth. The liquid sumps 10, as clearly shown in FIG. 8, all have the same width. Specifically, the shorter elongated holes 8B2 form the deeper liquid sump 10 together with the elongated holes 20B, while the longer elongated holes 8B1 form the shallower liquid sump 10 by themselves so that all the liquid sumps 10 may have the same volume. This structure permits the liquid inlets 5A to be formed, like the first embodiment, in a plurality of rows in the staggered fashion, thereby ensuring a maximum possible area of the liquid inlets 5A without any physical interference, and allowing the outlet nozzles 4A to be arranged in a dense array.

Figure 11:
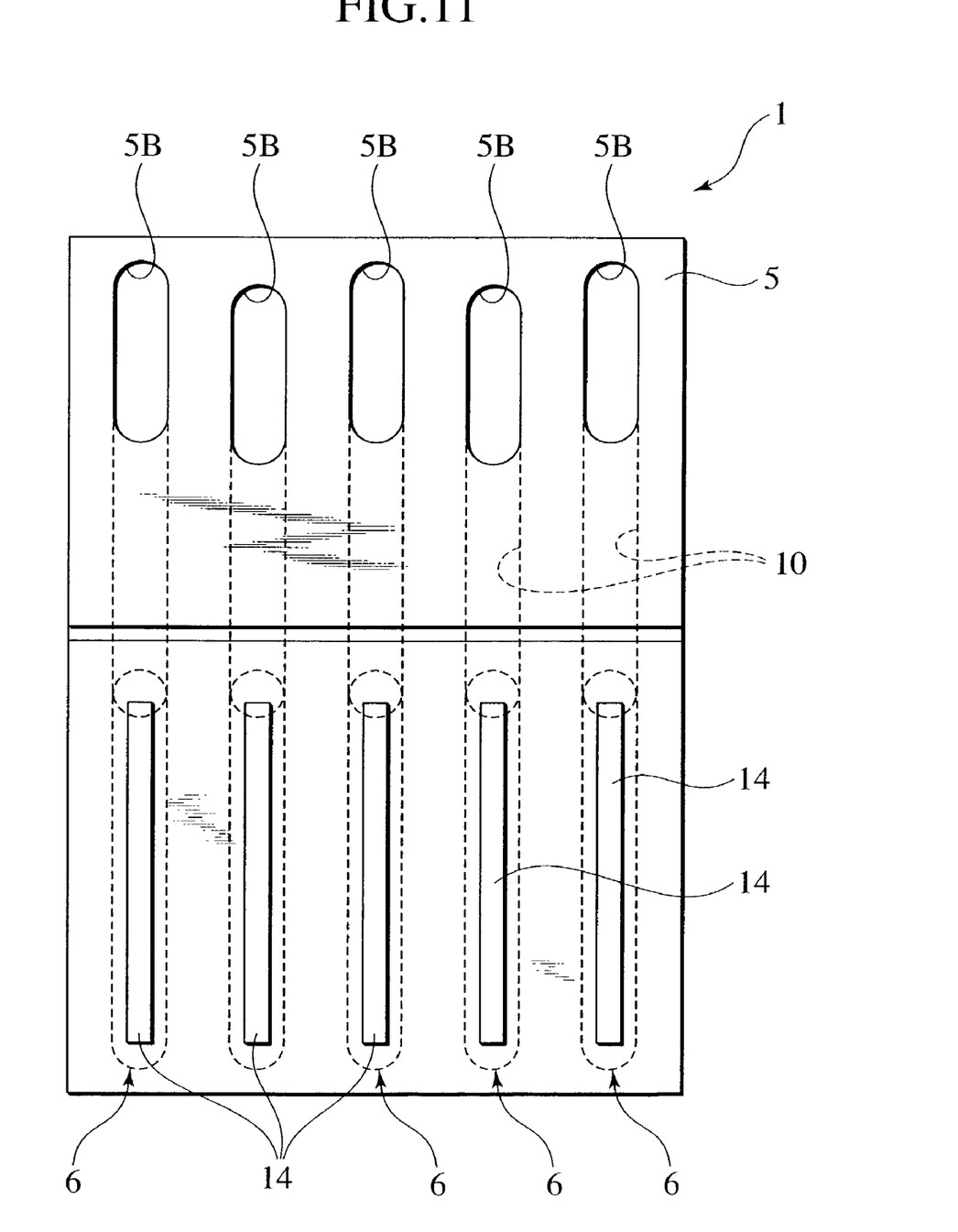
FIG. 11 is a top view which shows a first modification of the first and second embodiments.

FIG. 11 shows a first modification of the first and second embodiments.

The liquid drop emitter 1 has liquid inlets 5B whose opening is of an oval shape and smaller in width than the diameter of the liquid inlets 5A in the above embodiments, thereby allowing the micropipettes 6 to be arrayed in parallel at a shorter interval. Other arrangements are identical with those of the second embodiment, and explanation thereof in detail will be omitted here.

Figure 12:
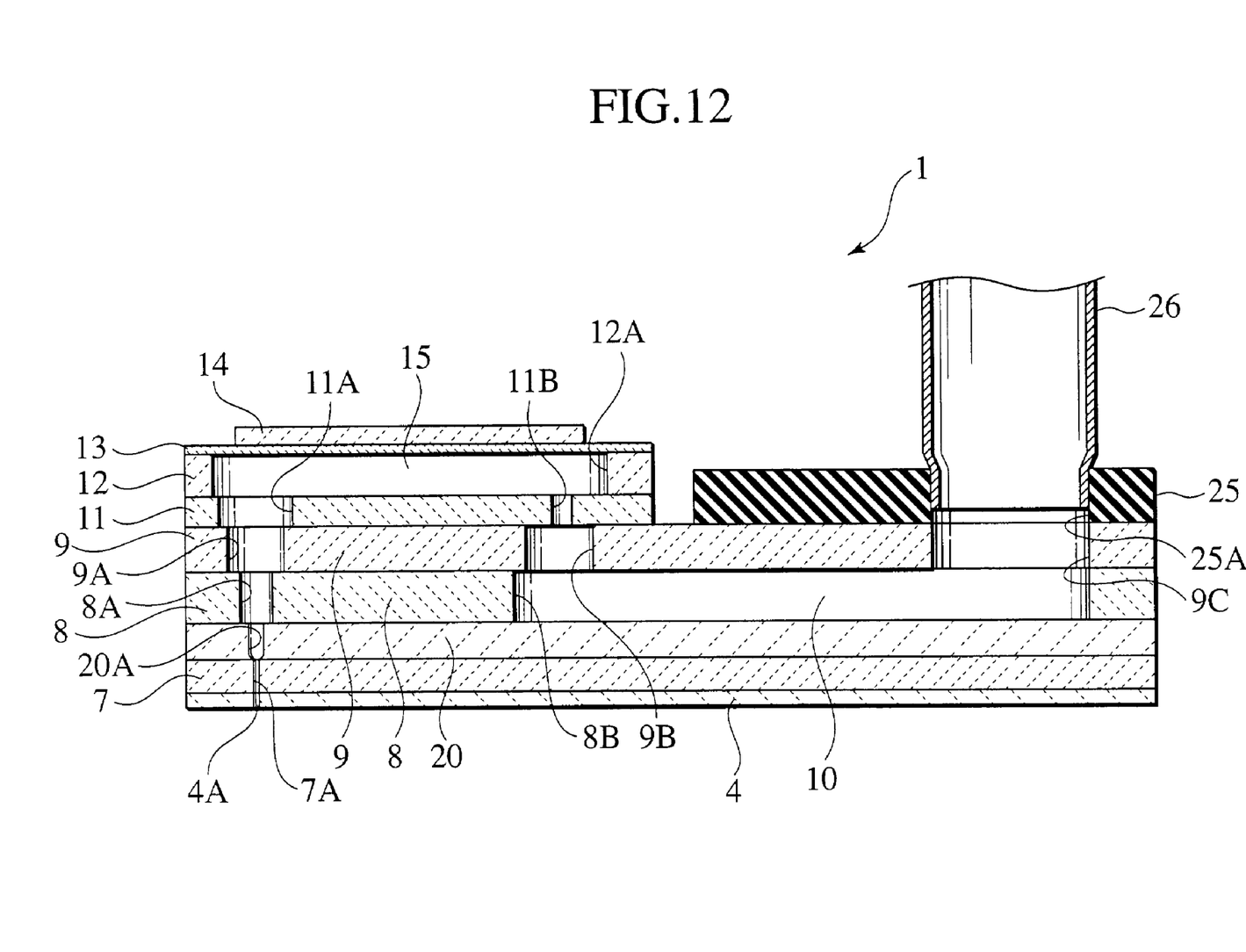
FIG. 12 is a vertical sectional view which shows a second modification of the first and second embodiments.

FIG. 12 shows a second modification of the first and second embodiments which is different therefrom only in a liquid inlet structure.

The liquid drop emitter 1 of this embodiment includes a rubber plate 25 and inlet tubes 26. The rubber plate 25 is bonded to the upper layer 9 of the flow-path base plate 2 and has formed therein holes 25A in which the inlet tubes 26 are fitted detachably. The inlet tubes 26 (i.e., the holes 25A) are arranged in rows in a staggered fashion, like the above embodiment, in the widthwise direction of the body of the liquid drop emitter 1. The inlet tubes 26 may be made of stainless steel or polypropylene. The liquid inlet structure of this embodiment allows the quantity of liquid put into the liquid drop emitter 1 to be increased, thereby resulting in a decrease in number of refilling operations.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims. For instance, the flow-path base plate 2, the actuator assembly 3, and the liquid inlet block 5A are made of ceramic materials, buy may alternatively be made of another material and have modified structures.

What is claimed is:

1. A liquid drop emitter comprising:

a plurality of micropipettes arrayed parallel to each other, each of said micropipettes defining a liquid flow path extending from a liquid inlet to an outlet nozzle through a liquid sump and a compression chamber to emit a drop of liquid, wherein the liquid inlets are arrayed in rows in a staggered fashion, the liquid flow paths are identical in volume with each other, and the compression chamber is separated from the liquid sump by a portion of the liquid flow path that decreases in cross-sectional area as it extends from the liquid sump to the compression chamber; and actuators, each of which works to compress a volume of one of the compression chambers to achieve emission of the drop of liquid from one of the outlet nozzles, wherein the liquid sumps of adjacent two of said micropipettes are different in width from each other.

2. A liquid drop emitter as set forth in claim 1, wherein said micropipettes are provided in the same body.

3. A liquid drop emitter as set forth in claim 1, wherein the liquid inlets are arrayed in at least one row in a staggered fashion within the row.

4. A liquid drop emitter as set forth in claim 1, wherein each liquid inlet has an axis that is parallel to a portion of the liquid flow path extending through the respective outlet nozzle.

5. A liquid drop emitter comprising:

a plurality of micropipettes arrayed parallel to each other, each of said micropipettes defining a liquid flow path extending from a liquid inlet to an outlet nozzle through a liquid sump and a compression chamber to emit a drop of liquid, wherein the liquid inlets are arrayed in rows in a staggered fashion, the liquid flow paths are identical in volume with each other, and the compression chamber is separated from the liquid sump by a portion of the liquid flow path that decreases in cross-sectional area as it extends from the liquid sump to the compression chamber; and actuators, each of which works to compress a volume of one of the compression chambers to achieve emission of the drop of liquid from one of the outlet nozzles, wherein the liquid sumps of adjacent two of said micropipettes are different in depth from each other.

6. A liquid drop emitter as set forth in claim 5, wherein said micropipettes are provided in the same body.

7. A liquid drop emitter as set forth in claim 5, wherein the liquid inlets are arrayed in at least one row in a staggered fashion within the row.

8. A liquid drop emitter as set forth in claim 5, wherein each liquid inlet has an axis that is parallel to a portion of the liquid flow path extending though the respective outlet nozzle.

* * * * *